US008075481B2

(12) United States Patent
Park et al.

(10) Patent No.: US 8,075,481 B2
(45) Date of Patent: Dec. 13, 2011

(54) INTERNAL RETRACTION SYSTEMS AND DEVICES

(75) Inventors: Adrian E. Park, Crownsville, MD (US); Charles F. Knapp, Georgetown, KY (US); Patrick N. Gutelius, Monroe, CT (US); Ralph Stearns, Bozrah, CT (US)

(73) Assignee: SurgiQuest, Inc., Milford, CT (US)

( * ) Notice: Subject to any disclaimer, the term of this patent is extended or adjusted under 35 U.S.C. 154(b) by 238 days.

(21) Appl. No.: 12/576,827

(22) Filed: Oct. 9, 2009

(65) Prior Publication Data

US 2010/0174150 A1   Jul. 8, 2010

Related U.S. Application Data

(63) Continuation-in-part of application No. 12/087,559, filed as application No. PCT/US2007/080948 on Oct. 10, 2007.

(60) Provisional application No. 60/850,496, filed on Oct. 10, 2006, provisional application No. 60/850,708, filed on Oct. 10, 2006, provisional application No. 61/195,793, filed on Oct. 10, 2008.

(51) Int. Cl.
*A61B 1/32* (2006.01)
*A61B 17/10* (2006.01)

(52) U.S. Cl. .................... 600/204; 600/218; 606/142

(58) Field of Classification Search .................. 600/204, 600/209, 210, 213, 217, 218, 226; 606/138, 606/139, 142–145
See application file for complete search history.

(56) References Cited

U.S. PATENT DOCUMENTS

2007/0282355 A1   12/2007   Brown et al.
2008/0114377 A1   5/2008    Shibata et al.

FOREIGN PATENT DOCUMENTS

WO   WO 2006-098994 A1   9/2006
WO   WO 2008-090978 A1   7/2008

OTHER PUBLICATIONS

International Search Report dated May 24, 2010.

*Primary Examiner* — Todd Manahan
*Assistant Examiner* — Ellen C Hammond
(74) *Attorney, Agent, or Firm* — Scott D. Wofsy; Edwards Wildman Palmer LLP

(57) ABSTRACT

An internal retraction system for use in minimally-invasive surgical procedures includes, among other features, an elongated applicator that has proximal and distal ends. The distal end of the applicator includes a grasper and the proximal end includes a mechanism or actuator for moving the grasper from an open position to a closed position. A plurality of anchor clips are slidably mounted on the elongated applicator and are initially in a stored position. Each clip includes spring biased upper and lower jaws for grasping tissue. The internal retraction system also includes a structure associated with the applicator for deploying the anchor clips from the stored position to a deployed position at a desired location. Moreover, the internal retraction system includes a mechanism associated with the applicator for removing the anchor clips from the deployed position and returning the clips to the stored position.

8 Claims, 26 Drawing Sheets

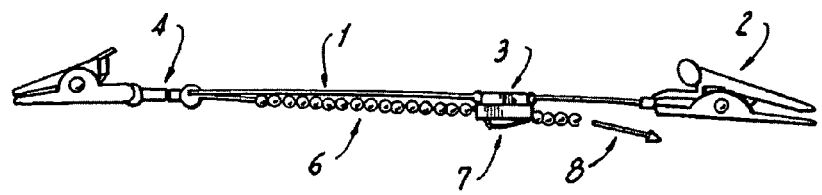
Fig. 1
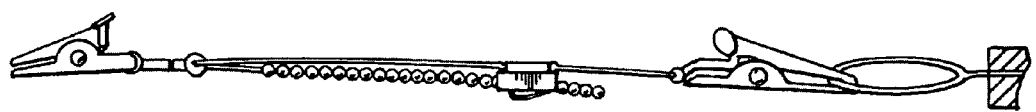
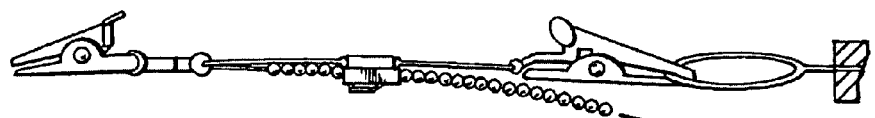
Fig. 2

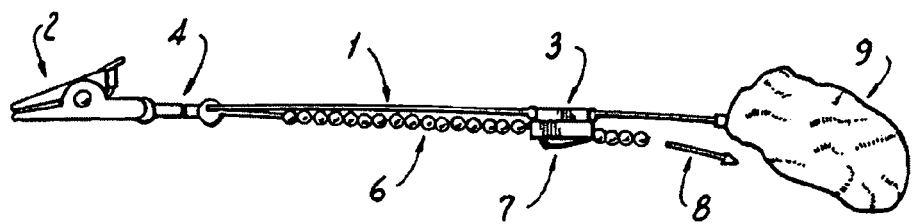
Fig. 9A
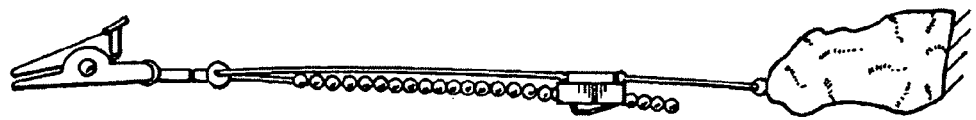
Length A
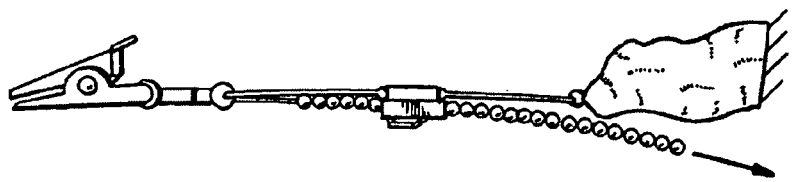
Length B
Fig. 9B

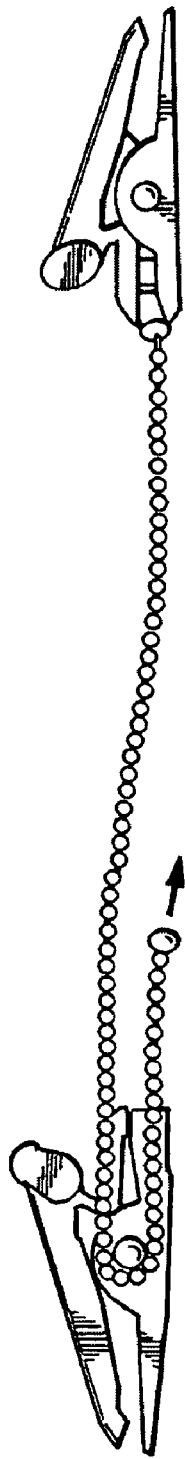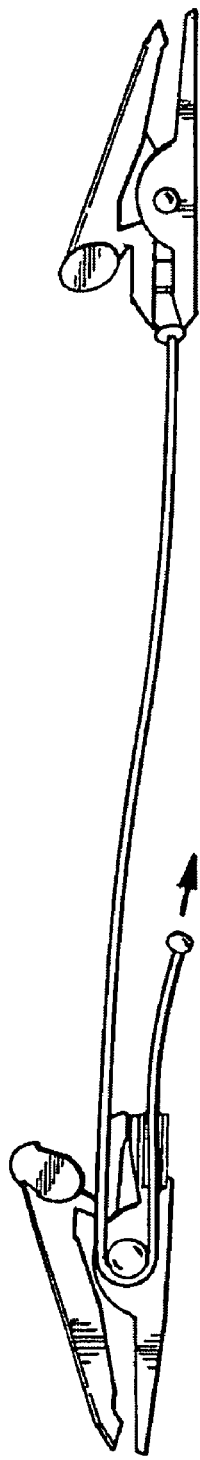
Fig. 10A
Fig. 10B

INTERNAL RETRACTION SYSTEMS AND DEVICES

CROSS-REFERENCE TO RELATED APPLICATIONS

This application is a continuation-in-part of U.S. patent application Ser. No. 12/087,559, filed on Jul. 9, 2008 and entitled Adjustable Line and Net Retractors, which is the U.S. national phase, pursuant to 35 U.S.C. §371, of International Application No. PCT/US2007/080948, published in English on Apr. 17, 2008 as International Publication No. WO 2008/045940 A2, which claims the benefit of U.S. Provisional Patent Application Ser. No. 60/850,496, filed Oct. 10, 2006, and U.S. Provisional Patent Application Ser. No. 60/850,708, filed Oct. 10, 2006. This application also claims the benefit of U.S. Provisional Patent Application Ser. No. 61/195,793, filed Oct. 10, 2008. Each of the aforementioned applications is incorporated herein by reference in its entirety.

BACKGROUND OF THE INVENTION

1. Field of the Invention

The invention relates to devices for use during surgical or non-surgical procedures in order to move items from the field of view or work space.

2. Background of the Related Art

Surgical procedures can require the retraction of tissue sections, tissue flaps, organs, organ flaps and the like so the field of view or work area is clear. For example, a segment of the liver may need to be held back in order to perform surgery on a segment of the intestine. This process can be demanding and typically can require an extra person to hold a conventional retractor. This procedure is even more challenging during minimally invasive surgery (MIS) where a trocar port and surgical technician may be devoted primarily to holding tissue back from the field of view or work area.

SUMMARY OF THE INVENTION

Retraction of items during any surgical or non-surgical procedure moves the items from the field of view or work space. The flexibility and compactness of a retraction device can make it suitable for surgery, especially minimally invasive surgery (MIS).

The present invention is directed to a tissue retraction system for use in MIS that includes, inter alia, an elongated applicator that has proximal and distal ends. The distal end of the applicator includes a grasper and the proximal end includes a mechanism or actuator for moving the grasper from an open position to a closed position. A plurality of anchor clips are slidably mounted on the elongated applicator and are initially in a stored position. Each clip includes spring biased upper and lower jaws for grasping tissue. The tissue retraction system also includes structure associated with the applicator for deploying the anchor clips from the stored position to a deployed position at a desired location. Moreover, the disclosed tissue retraction system includes a mechanism associated with the applicator for removing the anchor clips from the deployed position and returning the clips to the stored position.

It is envisioned that in certain embodiments, the tissue retraction system includes two anchor clips slidably mounted on the elongated applicator. Preferably, the two anchor clips are connected by a tether. It is envisioned that in a preferred embodiment, the tissue retraction system also includes a line connecting the two anchor clips and a length adjuster configured to allow the length of the line to be adjusted unidirectionally to separate tissue and to be selectively released.

In certain embodiments, the structure for deploying the anchor clips from the stored position to a deployed position at a desired location includes a tubular sleeve slidably positioned over the proximal end of the elongated applicator. Moreover, the mechanism for removing the anchor clips from the deployed position and returning the clips to the stored position can include a hook retractor.

The present invention is also directed to a method of retracting tissue using the previously described tissue retractor, as described herein below.

The present invention is also directed to new and novel grasper or clip constructions. In certain embodiments, the graspers have clamshell shaped upper and lower jaws which are particularly adapted for grasping tissue at various angles. Additionally, it is envisioned that the graspers or clips can include a lever arm that has a patterned recess formed therein for receiving a corresponding male projection formed, for example, on the end of a pair of forceps. The patterned recess allows that forceps to more securely grasp the lever arm(s) of the clip. In certain embodiments, that patterned recess has a six-pointed star appearance.

Additional objects, advantages and other novel features of the invention will be set forth in part in the description that follows and in part will become apparent to those skilled in the art upon examination of the foregoing or may be learned with the practice of the invention.

BRIEF DESCRIPTION OF THE DRAWINGS

So that those having ordinary skill in the art to which the subject invention pertains will more readily understand how to make and use systems and methods disclosed herein, embodiments thereof will be described in detail below with reference to the drawings, wherein:

FIG. 1 is a drawing depicting a side view of an adjustable retractor;

FIG. 2 is a drawing depicting a side view of an adjustable retractor in an initial state (A) and in a partial retracted state (B);

FIG. 9A is a drawing depicting a side view of an adjustable line retractor;

FIG. 9B is a drawing depicting a side view of an adjustable line retractor in the initial state (Length A) and in a partial retracted state (Length B);

FIG. 10A is a drawing depicting a side view of an adjustable line retractor including a line constructed from a ball chain;

FIG. 10B is a drawing depicting a side view of an adjustable line retractor including a line constructed from a plastic coated twisted wire;

DETAILED DESCRIPTION OF THE PREFERRED EMBODIMENTS

Figure 3A:
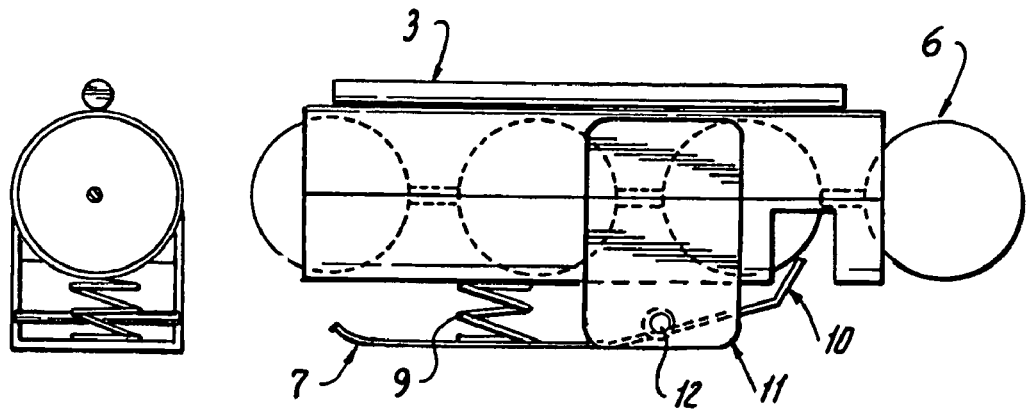
FIG. 3A is a drawing depicting a transparent side and end view of the one-way-pass-through/lock/release mechanism.
Figure 3B:
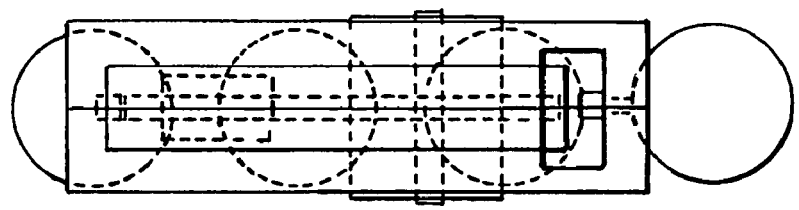
FIG. 3B is a drawing depicting a transparent bottom view of the one-way-pass-through/lock/release mechanism shown in FIG. 3A.

Devices for use during surgical or non-surgical procedures can move items from the field of view or work space. Retraction of items during any surgical or non-surgical procedure moves the items from the field of view or work space. The flexibility and compactness of a retraction device can make it suitable for surgery, especially minimally invasive surgery (MIS).

Adjustable retractors can control the position of internal organs, items and the like during surgery or other procedures. The adjustable line retractor can be a flexible line/clip arrangement capable of being attached to two items and shortened, within a pre-set force limit, to reduce the distance between the two items. The adjustable line retractor can include: 1) a flexible line with an atraumatic attachment clip at each end and 2) a one-way-pass-through/lock/release mechanism and a maximum-force-limit release mechanism between the two ends.

The device can be used, for example, to retract an internal organ from the field of view during surgery. The flexibility of the adjustable line retractor can allow it to be passed through a trocar and used as an adjustable retractor during minimally invasive surgery. The device can also be used for non-surgical applications.

The adjustable net retractor of the invention is a flexible net, with several line retractors around the netting perimeter, which can be used to hold back internal organs or tissue from the field of view during surgery. The adjustable net retractor can include a flexible net and adjustable line retractors which can deliver a distributed force load over the organ or item of interest during retraction. Attached to the perimeter of the flexible net can be several line retractors with atraumatic clips. At least two of the line retractors can be adjustable and contain a one-way-pass-through/lock/release mechanism and a maximum-force-limit release mechanism.

The device can allow the netting to be clipped to anchor points on one side and cinched tight by adjustable line retractors clipped to anchor points in other locations. Built-in force limiters can prevent tissue damage when the netting is cinched tight.

The flexibility of the adjustable net retractor allows it to be passed through a trocar and used as an adjustable net retractor during minimally invasive surgery. The adjustable net retractor can also be used for non-surgical applications where items can be held out of the field of view or just held in a specific location.

The adjustable line retractor or adjustable net retractor can eliminate the need for an extra person to hold tissue with a conventional retractor during surgery or MIS. A single operator can conduct the surgery and use and adjust the adjustable line retractor or the adjustable net retractor. The operator can use and adjust the adjustable line retractor or the adjustable net retractor using one hand only. In addition, a single entry port can be used for a surgical procedure, simplifying the procedure, reducing cost and reducing risk of complications including infection.

The primary components of an adjustable line retractor can include: an adjustable length line for example a non-elastic line, a length adjuster configured to allow the length of the line to be adjusted unidirectionally such as a one-way-pull through/lock/release mechanism, a safety-release pin or a maximum-force-limit mechanism and two tissue attachment tools such as clips at each end of the adjustable line retractor. The line can be threaded through a one-way-pull through/lock/release mechanism such that one end is available for pulling in order to shorten the retractor and pull an item back from the field of view or work area. With the cessation of pulling, the line can lock in place until the release mechanism is activated. The in-line maximum-force-limit mechanism ensures that tissue will not be damage by excessive force. Should a maximum force, for example two pounds, be exceeded and the safety-release pin released, it can be easily reloaded during a procedure. The features of such a device and its use to control the position of an item, especially in MIS, are new.

Referring to FIG. 1, comprising an adjustable length line constructed from a flexible material, with approximately half made from a woven filament, string or the like and the other half from a ball chain. Tissue attachment tools such as atraumatic grasping clips can be attached at each end and a length adjuster for example a one-way-pass-through/lock/release mechanism is located slightly right of center. The maximum-force-limit mechanism or safety-release pin can be attached to the left clip. The string can be tied to a hole on the right clip, passed through a small channel on top of the one-way-pass-through/lock/release mechanism and knotted at both sides of the channel. The string can then freely pass through the ring on the maximum-force-limit mechanism or safety-release pin located on the left clip. The ball chain part of the line passes through the lower channel of the one-way-pass-through/lock/release mechanism. The adjustable length line of the retractor can be made up of woven filament segment 1 which is tied to a ball chain segment 6.

During fabrication, the line can be tied to a hole in the right clip, passed through the top channel of the one-way-pass-through/lock/release mechanism 3, knotted on either side of the channel, and freely passed through the ring on the maximum-force-limit mechanism located on the left clip. The ball chain segment 6 of the line can be passed through the bottom channel of the oneway-pass-through/lock/release mechanism and a larger ball is clipped on the end to prevent the chain from sliding backwards through the lower channel when the release lever 7 is pressed. The larger ball also enables a better grip with forceps when the ball chain is pulled during retraction. The atraumatic clips 2 at each end, can be spring loaded and open when forceps are used to pinch the top and bottom back part of the clip. The upper rear part of the clip can be turned up slightly to minimize slippage of the forceps during squeezing. The atraumatic clips when pinched open, and then closed, can be used to grab tissue, suture loops and the like. With both clips attached to appropriate tissue points, for example, a force 8 applied as shown in FIG. 1 can cause the device to shorten the distance between attachment points, length A to B in FIG. 2.

Figure 5:
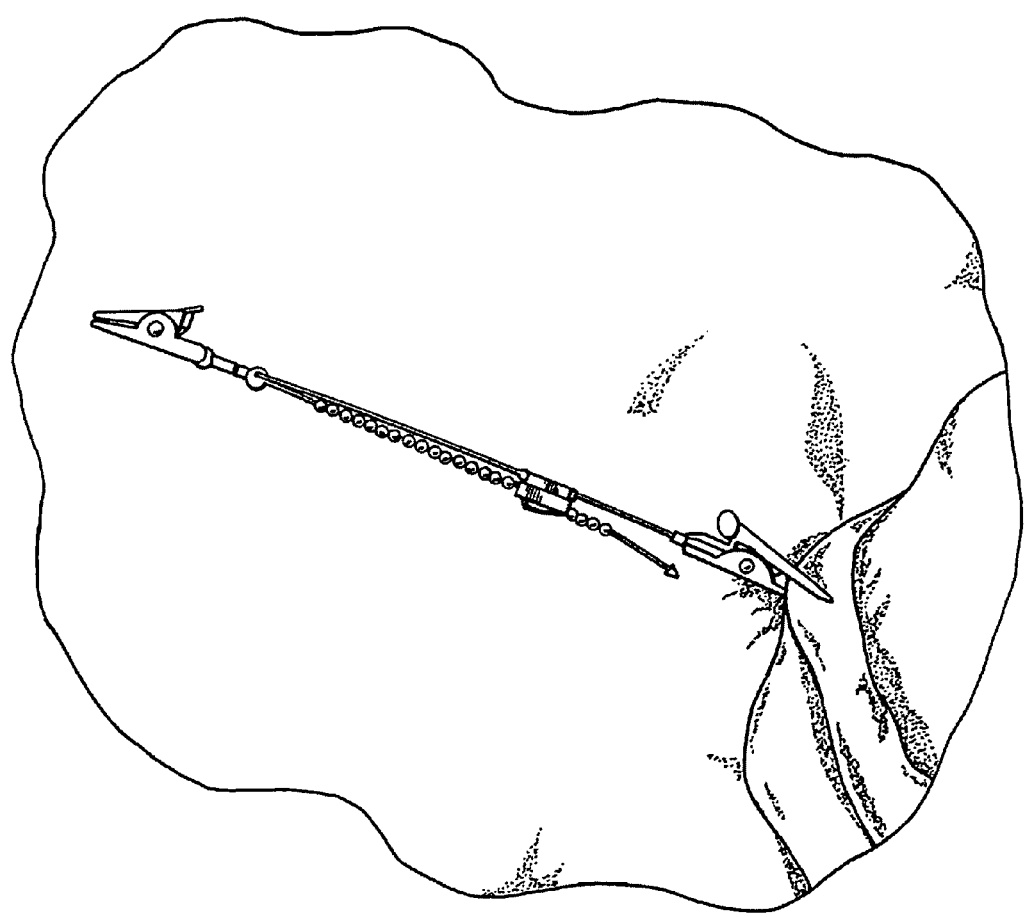
FIG. 5 is a drawing depicting application of an adjustable retractor retracting tissue during a surgical procedure.

With the cessation of the pull force 8, the ball chain can stay locked in position because of a spring loaded lever/fin which prevents the ball chain from moving. A cartoon of the adjustable line retractor attached to a suture loop at one end and holding back a tissue flap at the other is shown in FIG. 5. Use of forceps to squeeze the lever 7 on mechanism 3 will free the ball chain and allow for small adjustments or overall release of the retractor line. Removal of the retractor requires both clips to be freed from their appropriate attachments.

Referring to FIG. 3A, a length adjuster configured to allow the length of the line to be adjusted unidirectionally, for example a one-way-pull through/lock/release mechanism, can be defined by an upper channel for attachment of the line and a lower channel for the one way passage of the ball chain. A spring 9 loaded lever 7 with an angled tip 10 pivots on a pin 12 and allows the ball chain to travel only left to right for shorting the retractor as shown in the FIG. 3A because the curved tip can ride over the balls of the chain in that direction but hinders the ball of the chain from moving in the opposite direction, thereby producing tension in the retractor line once in use. Squeezing of the lever 7 with forceps can allow the balls of the chain to freely move in the opposite direction and reduce the tension in the line of the retractor.

Figure 4:
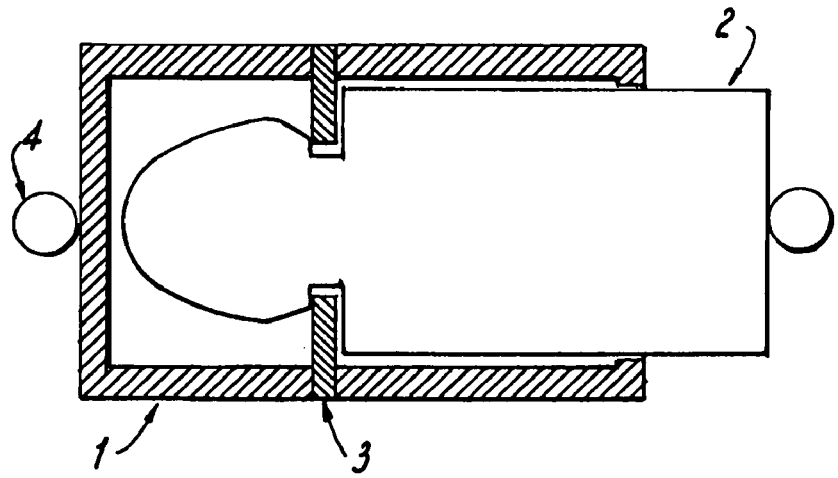
FIG. 4 is a drawing depicting a transparent side view of the maximum-force-limit or safety-release pin mechanism.

The safety-release pin or maximum-force-limit mechanism, FIG. 4, can include a circular tube 1 in which a pin 2 resides. The pin can have a smooth nose and a circular groove to accept flexible notch studs 3 that will lock in place when the pin is inserted. The notch studs and shape of the groove in the pin can be designed and calibrated to release the pin at a predetermined tension. Circular rings 4 are attached to the ends of the circular tube and pin so that a tissue clip can be attached to the circular tube end and the retractor line can be attached the pin.

Figure 6:
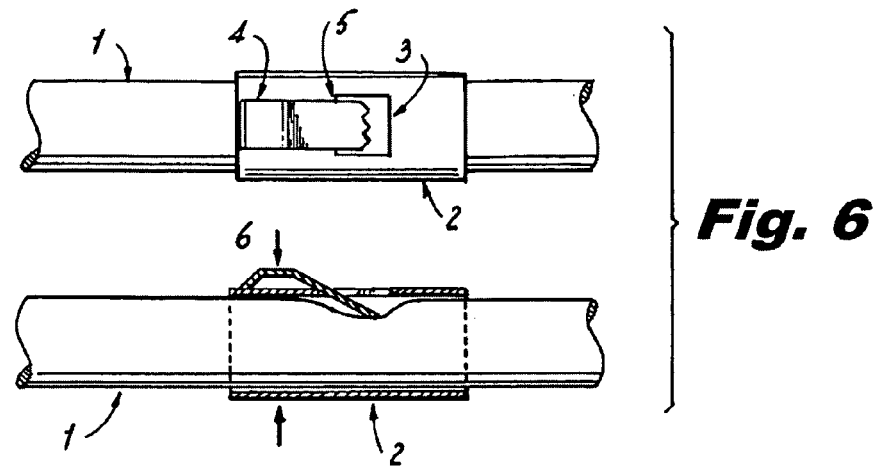
FIG. 6 is a drawing depicting side and top views of a one-way-pass-through/lock/release mechanism.

Although the adjustable line retractor can be used for any application in which a flap or item needs to be moved or held back from a field of view, including industrial applications, the main focus here is the ability of the adjustable line retractor to pass through a trocar, thereby making it uniquely suitable for minimally invasive surgery. Another structure for the one-way-pull through/lock/release mechanism is shown in FIG. 6. This structure can include of a polyfilament string 1 which passes through a circular channel 2 that incorporates a rectangular slot 3 through which a spring-loaded-serrated-edged-lever allows the polyfilament string to move from left to right, but not visa versa. The spring loaded lever pivots at the back edge 5 of the slot such that a pinching force 6 on the lever will cause the serrated end to move up thereby releasing the polyfilament and allowing it to move from right to left. As the pinching force is applied the back edge of the lever slides along the surface of the channel, thus no surfaces of discontinuity are available for the lever mechanism to get caught when removing the retractor through a trocar. It should be noted that the polyfilament can be replaced by any material that can withstand the forces of the serrated edges of the level to stop movement in one direction without being severed.

Figure 7:
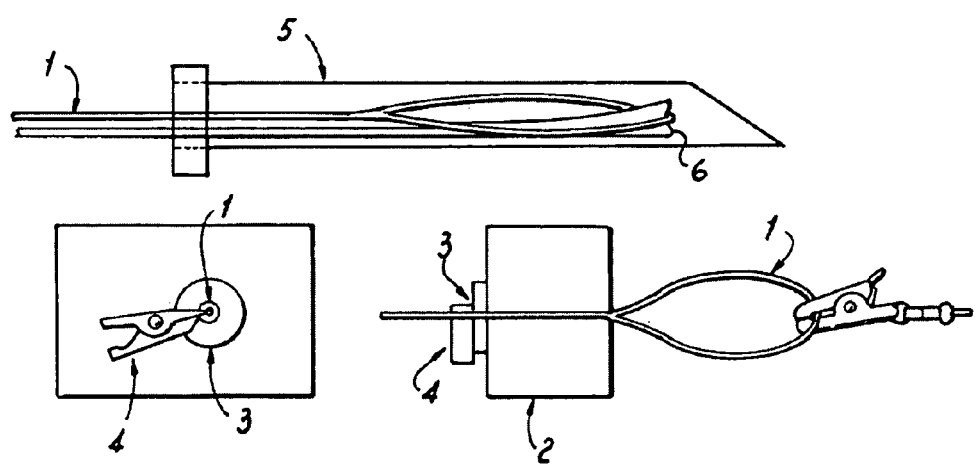
FIG. 7 is a drawing depicting a transparent side view of the anchor loop applier and a front and side view of the anchor loop inserted through simulated abdominal tissue.

The anchor loop, FIG. 7, can include a monofilament 1 (or other filament) with a long tail. The anchor loop can be inserted through the abdominal wall 2, for example, by a thin trocar applicator (top drawing of FIG. 7). The anchor loop is held in place by washer 3/clip 4 arrangement such that any tension on the anchor loop by the line retractor (see FIG. 6) can be resisted by the washer/clip. The washer distributes the load over the abdominal surface and the clip keeps the monofilament from slipping. The trocar applier includes two major elements: the main trocar barrel 5 with a needle beveled end and a loop holder 6. When the trocar is inserted through the abdominal wall, for example, the loop holder is pushed forward thereby inserting the anchor loop. After the trocar and loop holder are removed the washer/clip is attached to provide a wall anchor for the line retractor. The primary components of an adjustable net retractor can include: a sheet, for example an elastic netting, at least two tissue attachment tools, for example atraumatic non-adjustable tissue clips, and at least two adjustable line retractors. The two atraumatic non-adjustable clips can be attached around the perimeter of the netting, preferably on two corners. The two adjustable retractors can be located opposite of the two non-adjustable clips.

Figure 8:
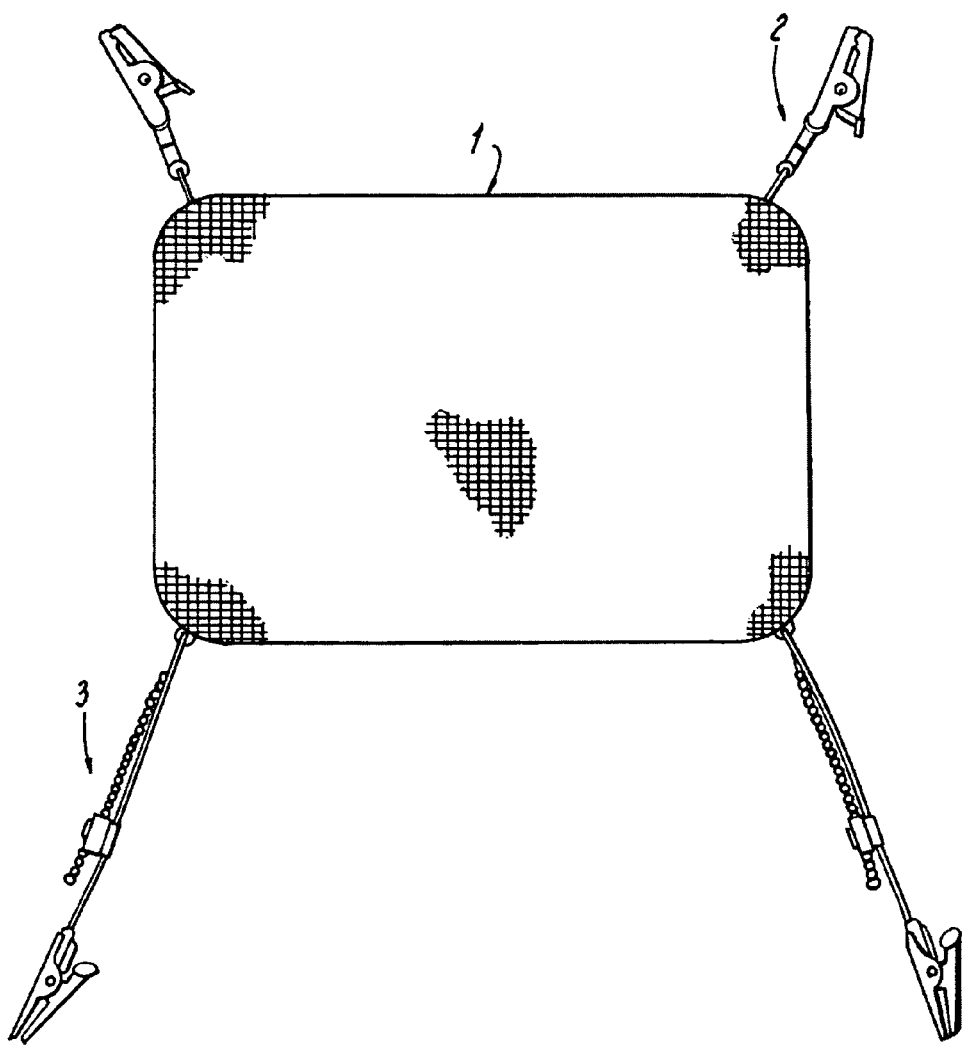
FIG. 8 is a drawing depicting a top view of an adjustable net retractor.

The adjustable line retractor can include a non-elastic line, a one-way-pull through/lock/release mechanism, a maximum-force-limit mechanism and an atraumatic clip at the end not attached to the netting. The non-elastic line can be threaded through the one-way-pull through/lock/release mechanism such that one end is available for pulling thereby causing the line to shorten and the net to be cinched against the organ of interest. With cessation of pulling on the line, the line will lock in place with tension remaining in the line retractor thereby keeping the net cinched against the organ and away from the surgical work area. With the cessation of pulling, the line will stay locked in place until the release mechanism is activated. The in-line maximum-force-limit mechanism assures that tissue or organs will not be damage by excessive tensile or compressive force loads. Should a preset maximum force, for example two pounds, be exceeded and the pin released, it can be easily reloaded during a procedure. The features of such a device and its use to control the position of an item, especially in MIS, are new. The adjustable net retractor is shown in FIGS. 8 and 9. Referring to FIG. 8, an adjustable net retractor can include a sheet, for example an elastic net, which can be shaped, for example, rectangular in shape, with at least two tissue attachment tools for example atraumatic non-adjustable tissue clips and at least two adjustable line retractors. The device can include an elastic net 1 (which can be rectangular in shape), in FIG. 8, with at least two atraumatic tissue clips 2 on the perimeter at the corners and at least two adjustable line retractors 3 on the perimeter at opposite corners from the non-adjustable retractors. The adjustable line retractor attached to netting 9 is shown in more detail in FIG. 9. The adjustable net retractor can include an adjustable length line, which can be constructed from a flexible material, with approximately half made from a woven filament and the other have from a ball chain.

Tissue attachment tools, for example Atraumatic grasping clips, can be attached at one end and a length adjuster, for example a one-way-pass-through/lock/release mechanism is located slightly right of center. The safety-release pin or maximum-force-limit mechanism can be attached to the left clip. The string can be tied to a hole on the right clip, passed through a small channel on top of the one-way-pass-through/lock/release mechanism and knotted at both sides of the channel. The string then freely passes through the ring on the maximum-force-limit mechanism located on the left clip. The ball chain part of the line passes through the lower channel of the one-way-pass-through/lock/release mechanism. The line of the adjustable retractor can be made up of woven filament segment 1, in FIG. 9A which is tied to a ball chain segment 6. During fabrication, the line can be tied to a hole in the right clip, passed through the top channel of the one-way-pass-through/lock/release mechanism 3, knotted on either side of the channel, and freely passed through the ring on the maximum-force-limit mechanism located on the left clip. The ball chain segment 6 of the line is passed through the bottom channel of the one-way-pass-through/lock/release mechanism and a larger ball is clipped on the end to prevent the chain from sliding backwards through the lower channel when the release lever 7 is pressed. The larger ball also enables a better grip with forceps when the ball chain is pulled during retraction.

The atraumatic clip 2 at one end, is spring loaded and open when forceps are used to pinch the top and bottom back part of the clip. The upper rear part of the clip is turned up slightly to minimize slippage of the forceps during squeezing. The atraumatic clip when pinched open, and then closed, can be used to grab tissue, suture loops and the like. With the clip attached to appropriate tissue points, for example, a force 8 applied as shown in FIG. 9A can cause the device to shorten the distance between attachment points, length A to B in FIG. 9B. With the cessation of the pull force 8, the ball chain will stay locked in position because of a spring loaded lever/fin which prevents the ball chain from moving. Use of forceps to squeeze the lever 7 on 3 will free the ball chain and allow for small adjustments or overall release of the retractor line.

FIG. 10A is a side view of the adjustable line retractor comprising a line constructed from a ball chain. The hold/release mechanism and the safety-release pin may be located in the handles of the tissue clip. The ball and chain can be rotated around the center shaft of the clip providing a larger radius of curvature. FIG. 10B is a side view of the adjustable line retractor comprising a line constructed from a plastic coated twisted wire. The plastic coated twisted wire allows the teeth in the release mechanism to hold very well.

Figure 11A:
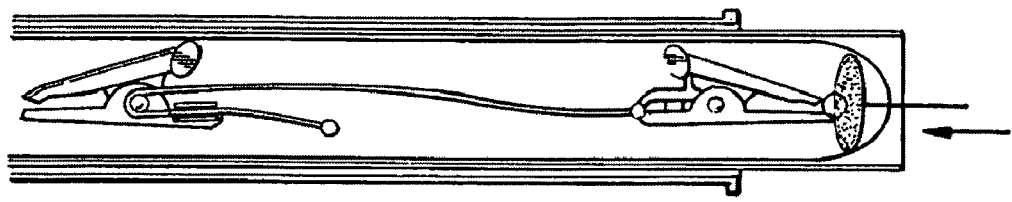
FIGS. 11A, 11B, and 11C are drawings depicting side views of an adjustable line retractor enclosed in a movable sleeve and inserted in a trocar.
Figure 11B:
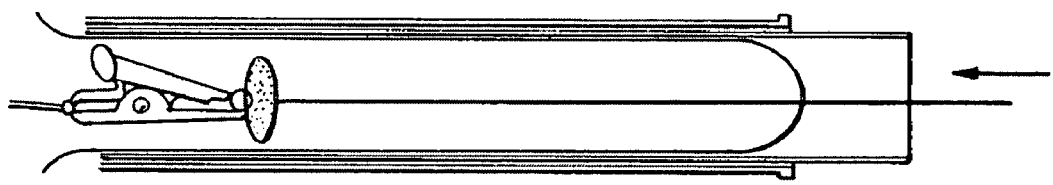
Figure 11C:
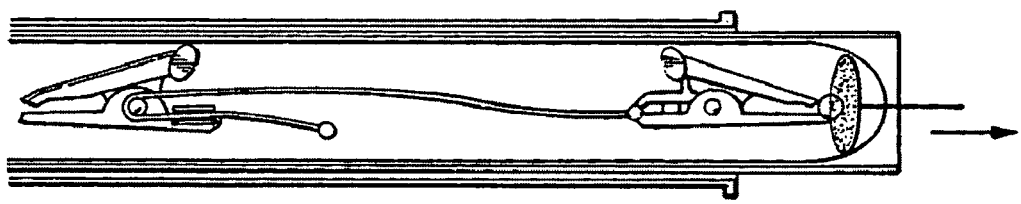

FIGS. 11A, 11B, and 11C are side views of an adjustable line retractor enclosed in a movable sleeve and inserted in a trocar. Either the adjustable line retractor or the adjustable net retractor may have a thin flexible sleeve around them for ease of passing through a trocar for introducing or retrieving units. The sleeve can be designed to flare to ensure smooth introduction of the line retractor in the trocar. A plunger allows introducing or pulling the line retractor in or out of the trocar.

Figure 12:
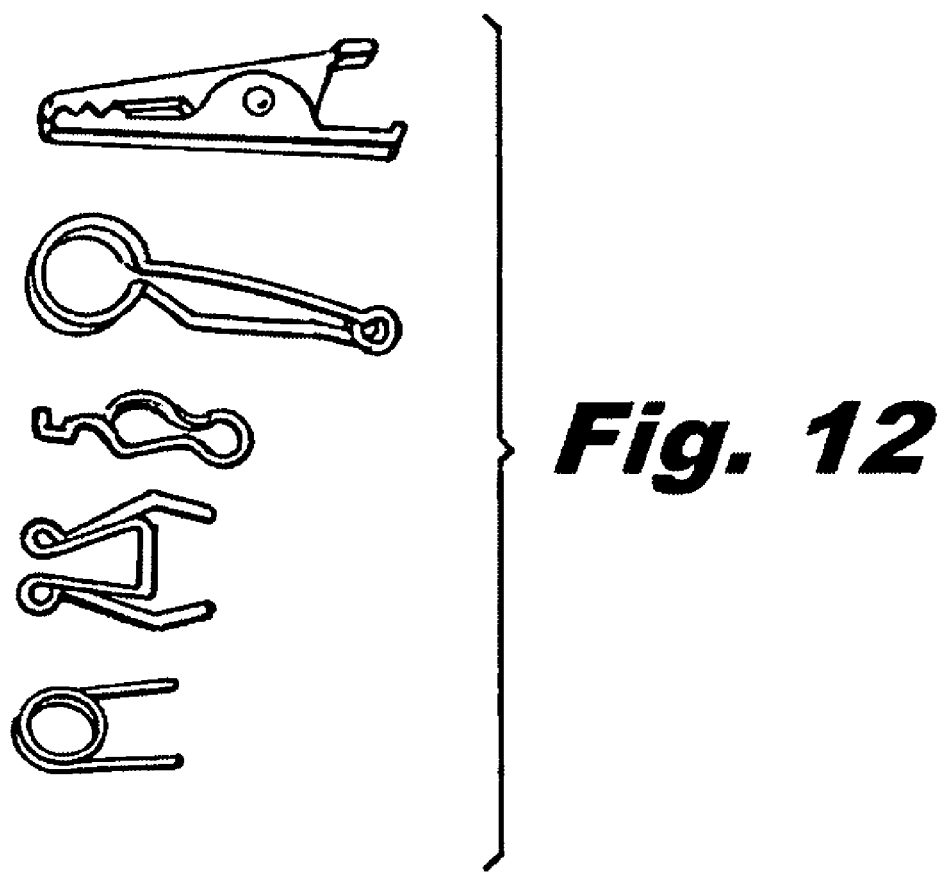
FIG. 12 shows various tissue attachment tools.

FIG. 12 shows various tissue attachment tools that can be used. The tissue attachment tools may be of various styles and tips. For general purposes, standard alligator type clips may suffice with torque springs and tips lined with a tooth/groove configuration designed to grasp the material during the retracting process without producing damage. Other clip designs may include a low profile concave-convex jaw design, parallel sided jaw design or clips configured to have tips with tissue contacting surfaces to mimic any style of surgical graspers.

Figure 13A:
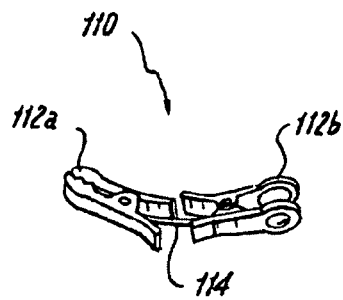
FIGS. 13A-13C show various additional tissue retraction devices.
Figure 13B:
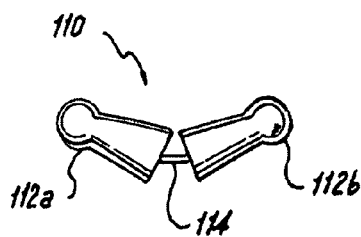
Figure 13C:
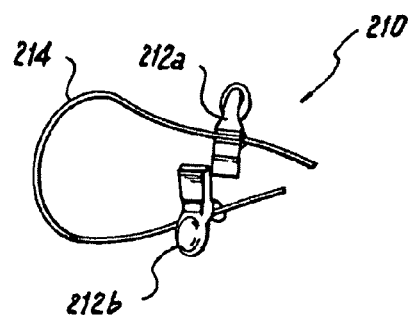

FIGS. 13A-13C illustrate additional line retractor constructions of the present invention. In FIGS. 13A and 13B, there is illustrated a retractor 110 which includes attachment tools/clips 112a and 112b connected together using a wire tether 114. Similarly, FIG. 13C also discloses a retractor 210 which includes attachment tools/clips 212a and 212b connected together using a wire tether 214. In both embodiments, the wire 114/214 is connected to the clips 112/212 such that when the wire is pulled with forceps, for example, the lever arms of the clips are pinched together so as to open the jaws and release any tissue trapped therebetween.

Figure 14A:
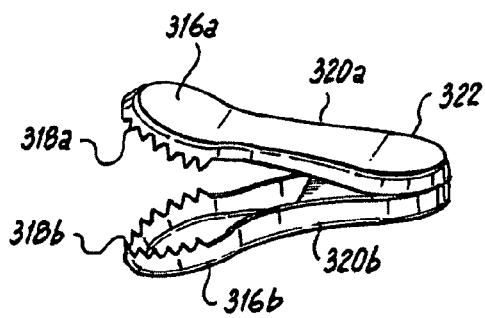
FIGS. 14A and 14B illustrate further grasper constructions of the present invention.
Figure 14B:
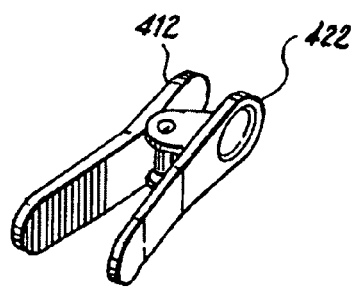

FIGS. 14A and 14B disclose new and novel grasper or clip constructions. In FIG. 14A, there is illustrated a grasper or clip 312 which is shown with its jaws 316a/316b spaced apart. Jaws 316a/316b are typically biased in the closed position like standard alligator clips. Unlike conventional clips, the jaws 316a/316b of clip 312 are clamshell shaped and are particularly adapted for grasping tissue at various angles. Because of the unique curved leading edge 318a/318 of the jaws 316a/316b, clip 312 can grab a hold of tissue even when it is presented to the tissue at an acute angle.

Clip 312 also includes upper and lower lever arms, 320a and 320b respectively. Upper lever arm 320 has a patterned recess 322 formed in its top surface for receiving a corresponding male projection formed, for example, on the end of a pair of forceps. The patterned recess 322 allows forceps to more securely grasp the lever arms of the clip. FIG. 14B illustrates a further clip embodiment, 412, having a patterned recess 422 formed in at least one of the lever arms. As shown in FIGS. 14a and 14b, the patterned recess 322/422 has a six-pointed star appearance. Those skilled in the art will readily appreciate other configurations, for example, similar to those used in Allen wrenches, can be provided without departing from the scope of the present invention.

Figure 15:
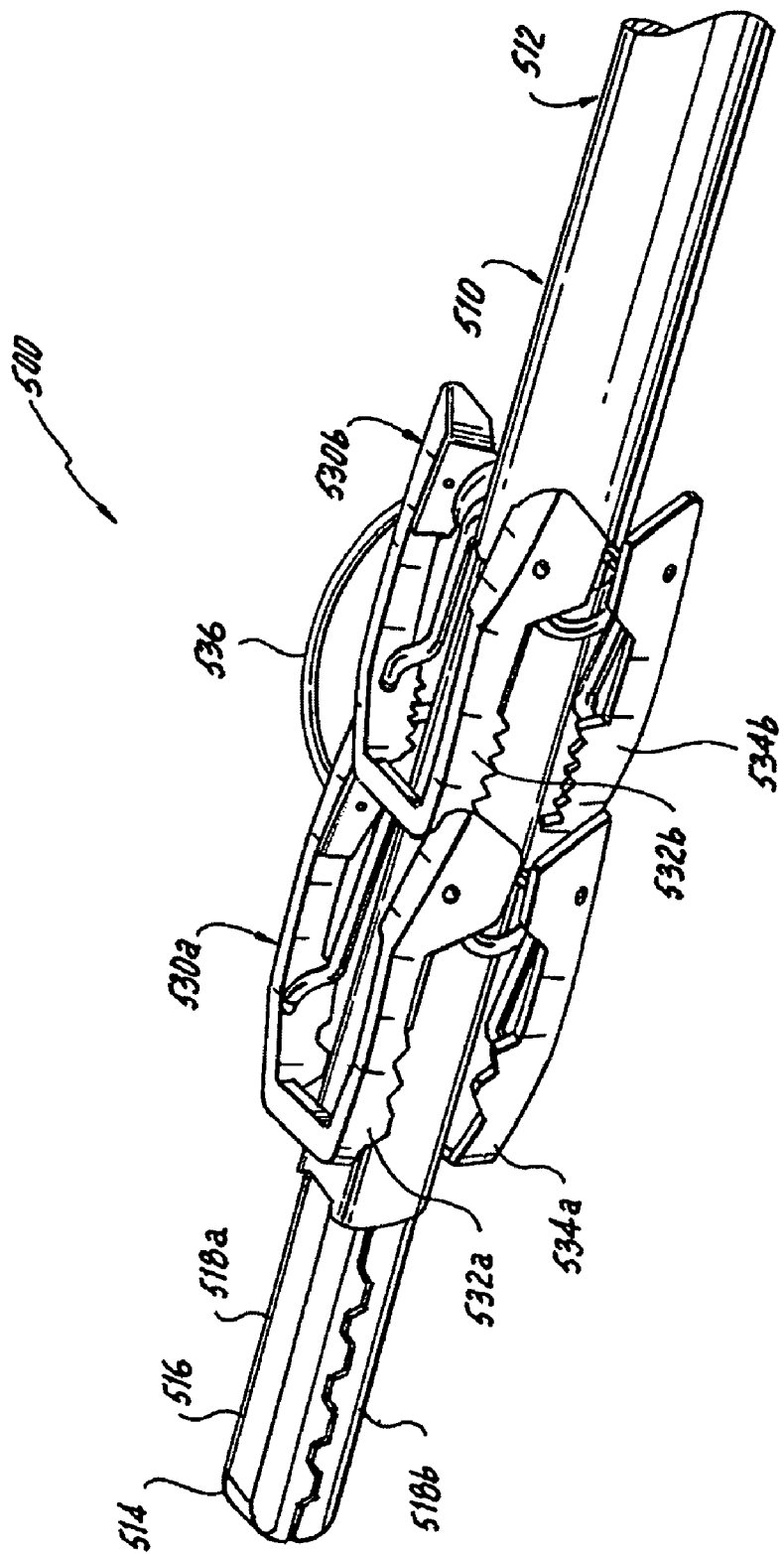
FIGS. 15-30 illustrate a device and method for deploying a line retractor that includes two tissue attachment tools tethered together.

Referring now to FIGS. 15 through 30, there is illustrated a tissue retraction system that is constructed in accordance with the present invention and designated generally by reference numeral 500. Retraction system 500 includes, inter alia, an elongated applicator 510 that has proximal and distal ends, 512 and 514 respectively. The distal end 512 of the applicator 510 includes a grasper 516 (or pre-grasper) having upper and lower jaws 518a/518b. The proximal end 512 of the applicator 510 includes a mechanism or actuator (not shown) for moving the jaws 518a/518b of the grasper 516 from an open position to a closed position. In FIG. 15, the jaws 518a/518b of the grasper 516 are shown in the closed position and in FIG. 16, the jaws 518a/518b are in the open position.

Two anchor clips 530a/530b are slidably mounted on the elongated applicator 510 and are initially in a stored position. Each clip 530 includes spring biased upper 532 and lower 534 jaws for grasping tissue. The clips 530a/530b are connected through tether 536. In alternative embodiments, the tissue retraction system can include a line connecting the two anchor clips and a length adjuster, as described supra, which is configured to allow the length of the line to be adjusted unidirectionally to separate tissue and to be selectively released.

The tissue retraction system 500 also includes a mechanism associated with the applicator for deploying the anchor clips 530a/530b from the stored position to a deployed position at a desired location. This mechanism is not shown in the figures, but those skilled in the art will readily appreciate that a simple tubular structure can be slid over the applicator from the proximal end toward the distal end. When the tubular structure contacts the proximal end of clip 530b it will begin to slide the clips 530a/530b off applicator 510.

Figure 16:
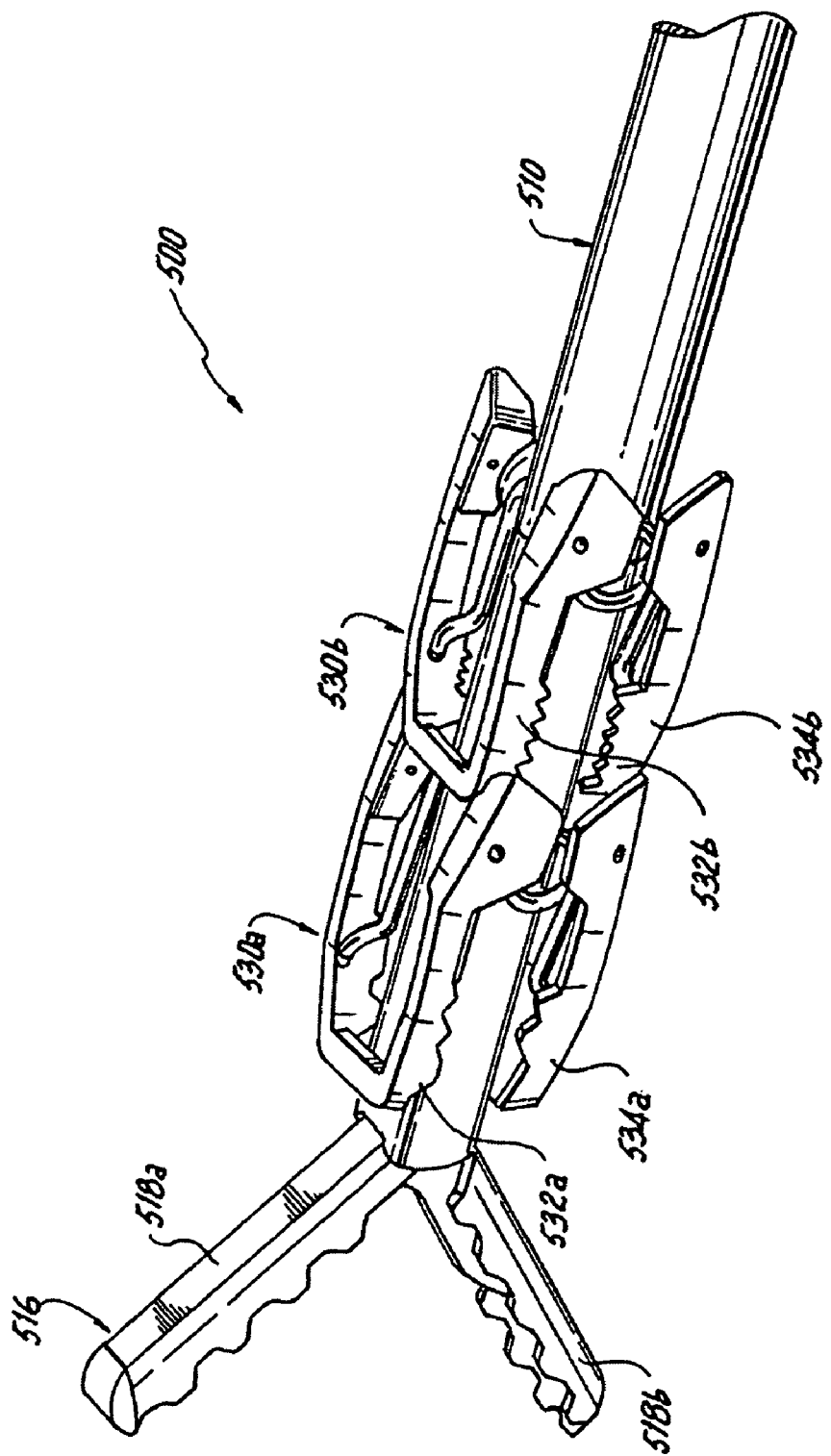

FIGS. 15-30 illustrate a representative method for using tissue retraction system 500. FIG. 15 illustrates the retraction system 500 prior to its use in, for example, minimally invasive surgery. In this configuration, the retraction system 500 can be inserted into a trocar tube and the distal end of grasper 516 is placed adjacent to the tissue, structure or item to be clipped. As shown in FIG. 16, once the retraction system is positioned at the desired location, the jaws 518a and 518b of grasper 516 are opened in order to allow tissue to be positioned therebetween. Next the jaws 518a/518b of grasper 516 are closed thereby grasping the tissue.

Figure 17:
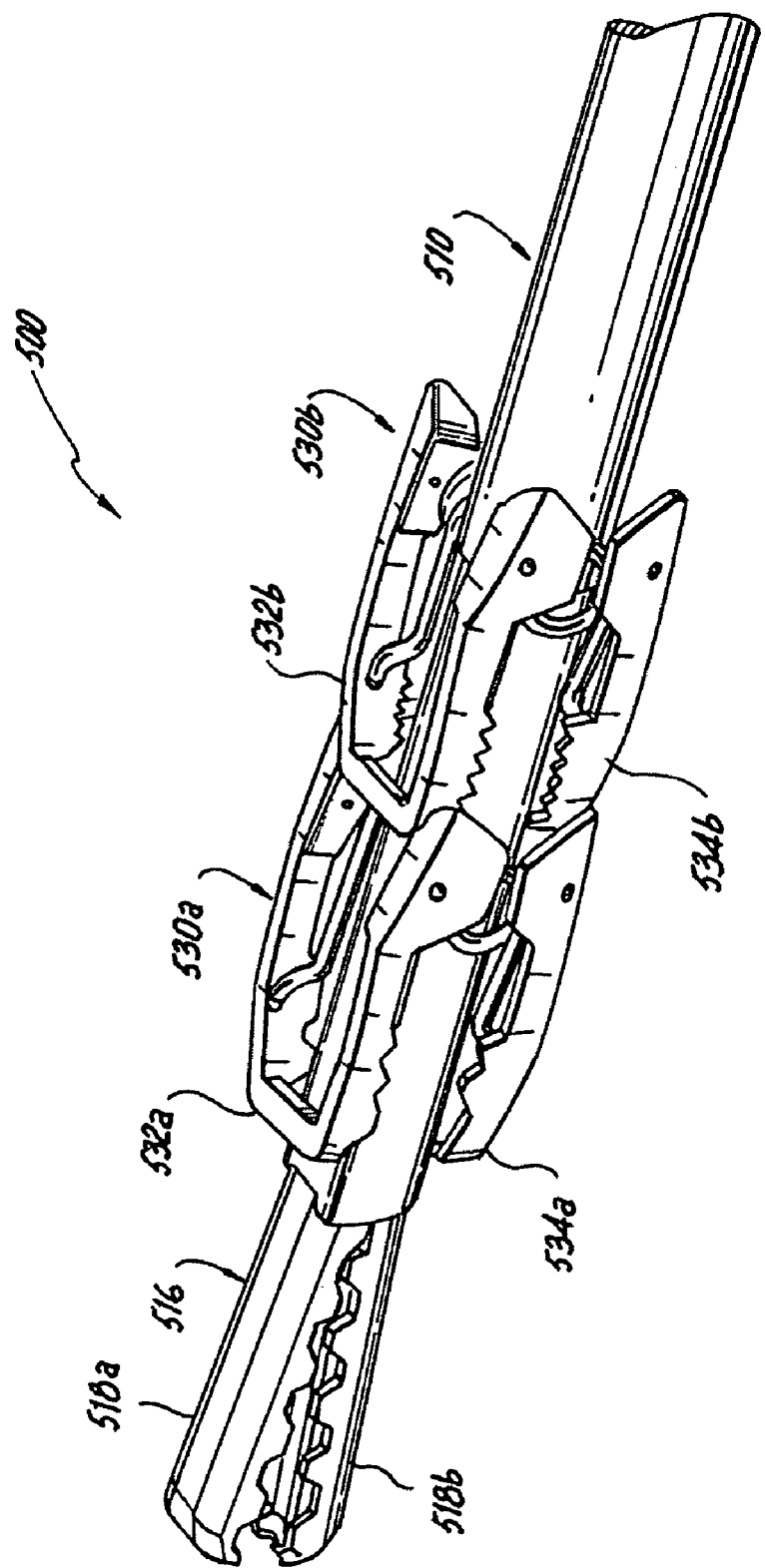
Figure 18:
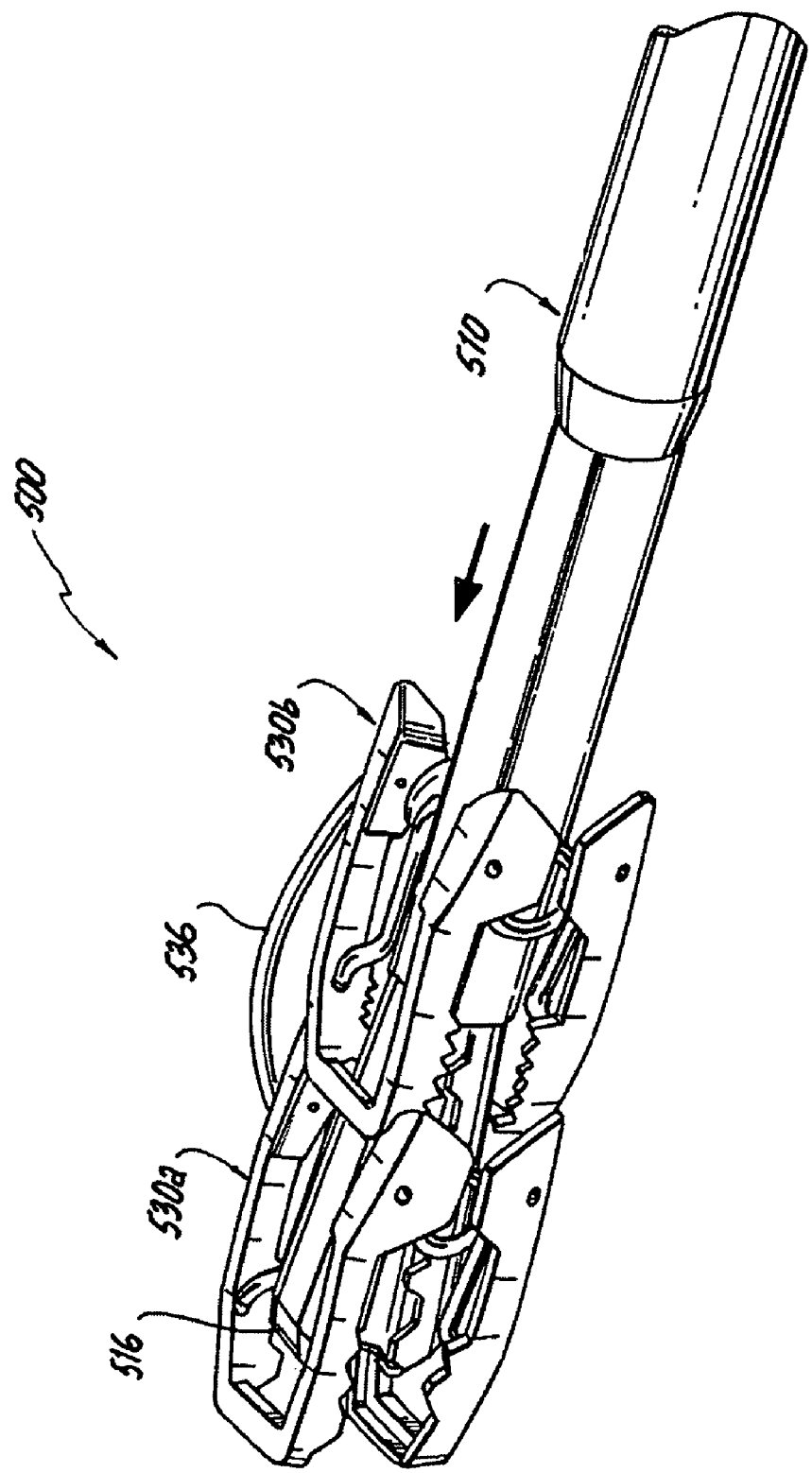
Figure 19:
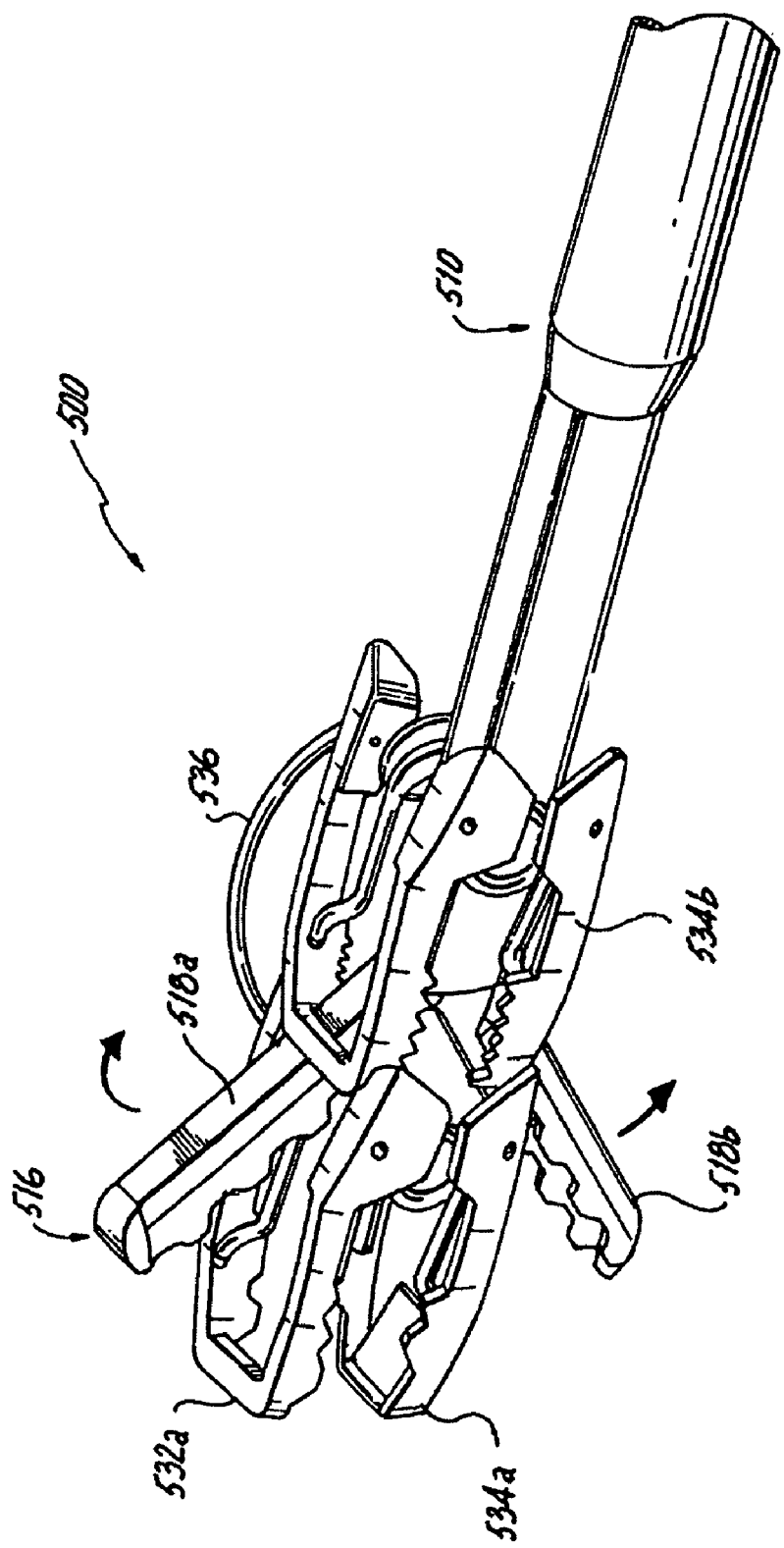
Figure 20:
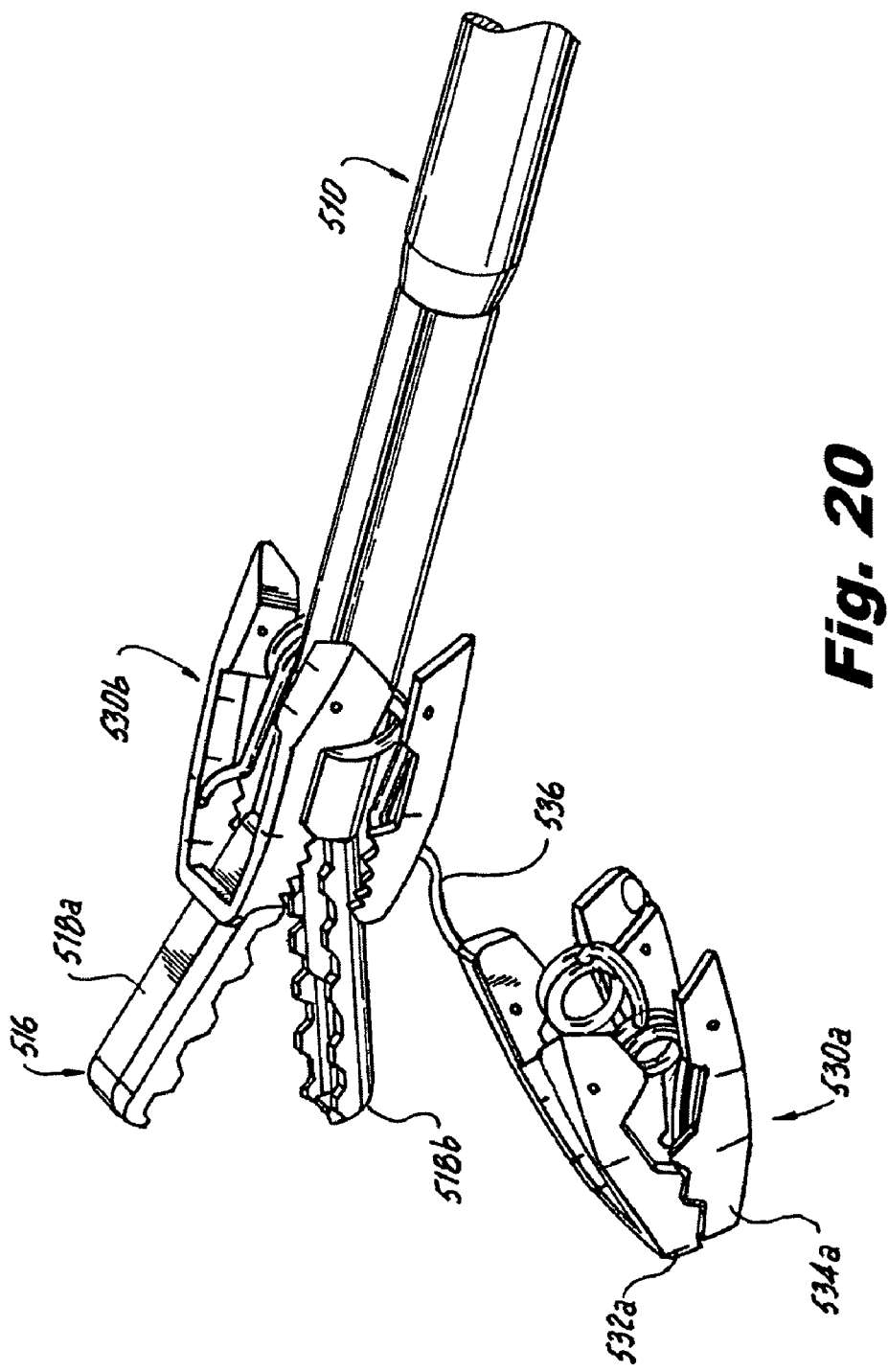

In FIG. 17 the jaws 518a and 518b of grasper 516 are shown partially open to simulate that tissue is being pinched the jaws. Next, the clips 530a and 530b are advanced from the stored position using for example, a pusher tube (not shown). While positioned on the applicator 510, the jaws 532/534 of the clips 530 are biased opened. When the lead clip 530a is completely pushed off the applicator 510 it contacts the tissue held by the grasper 516 and clamps down on this tissue. Next, as shown in FIG. 19, the jaws 518a/518b of the grasper 516 are opened so as to release the tissue held by the grasper.

Figure 21:
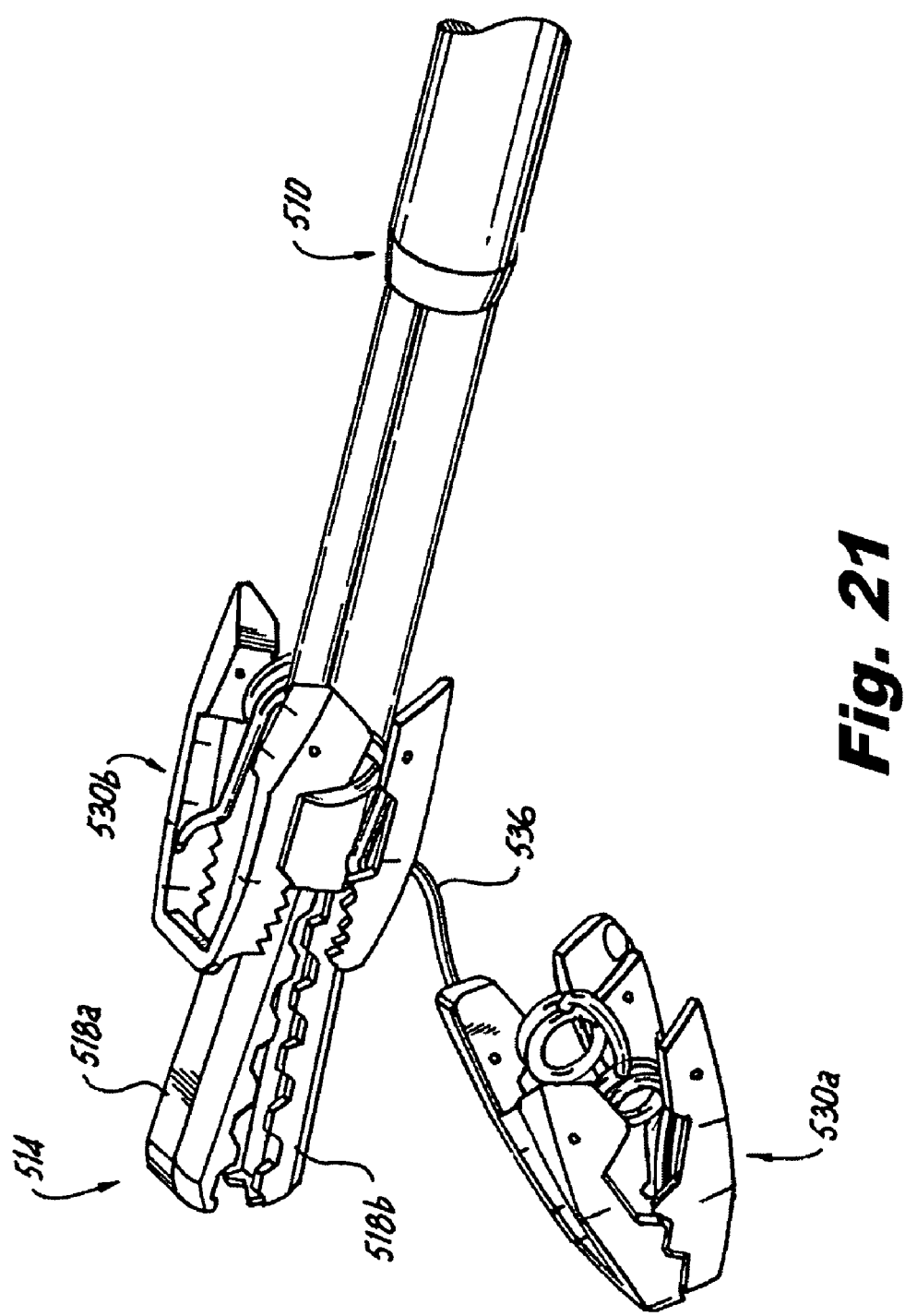
Figure 22:
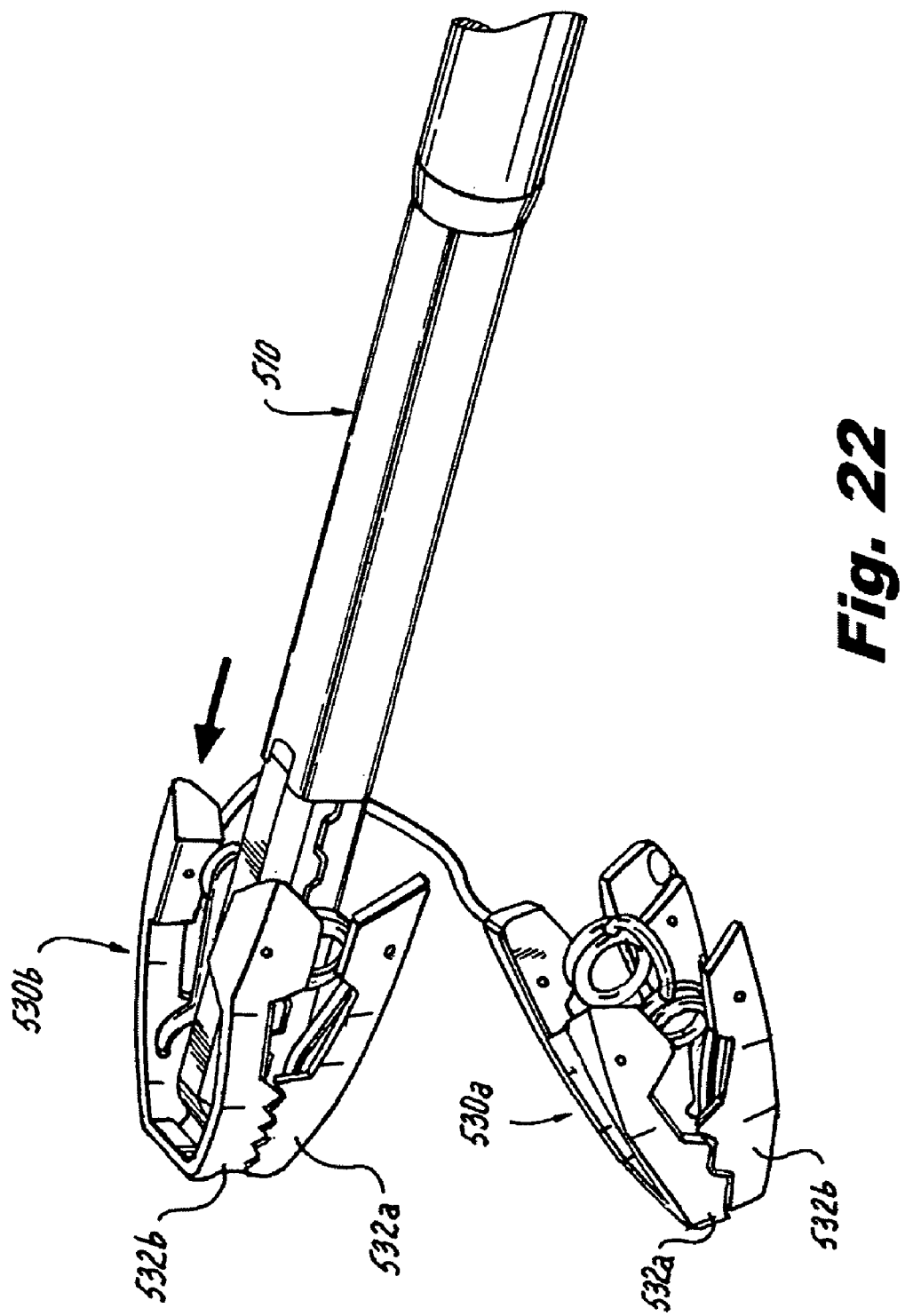
Figure 23:
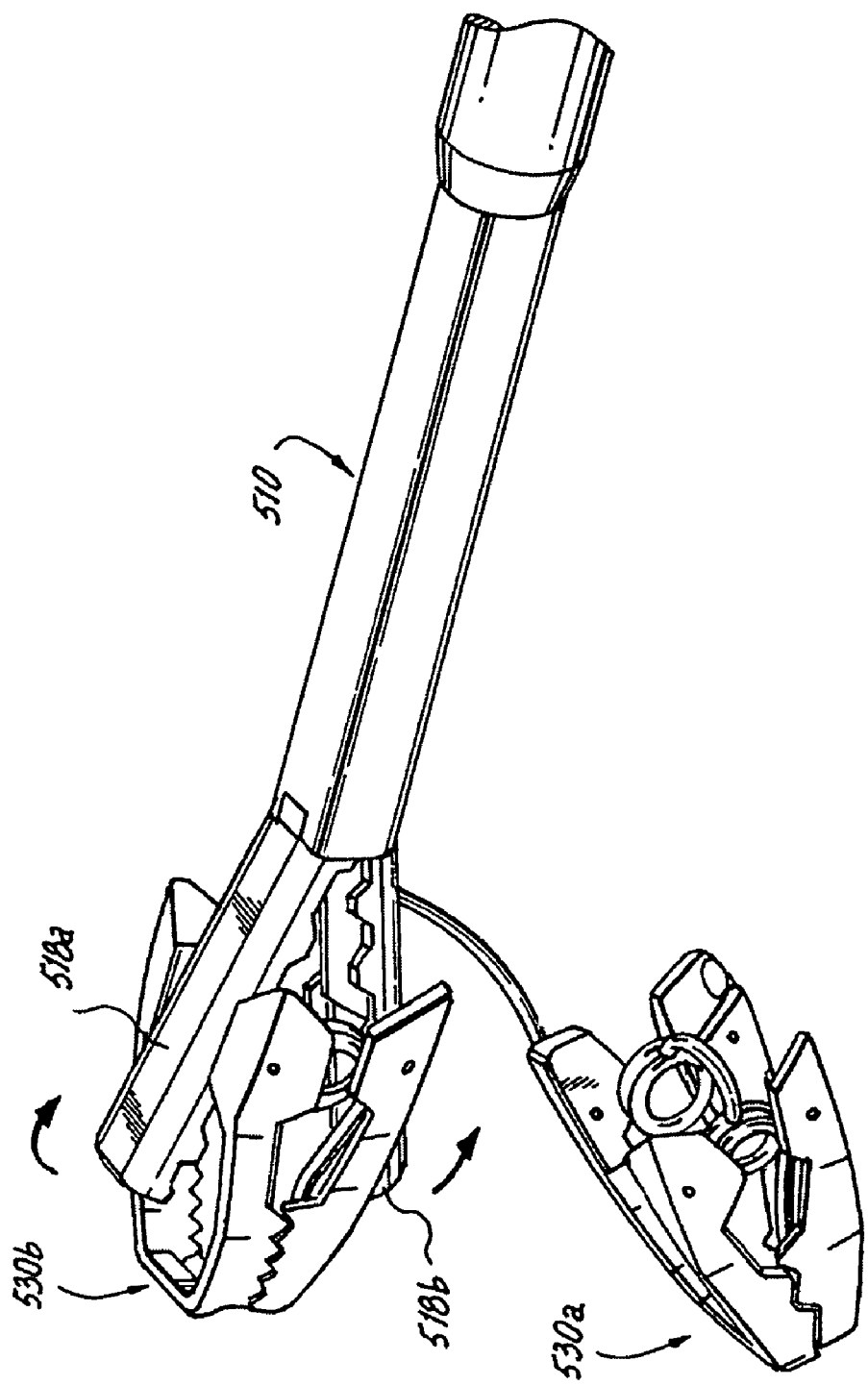
Figure 24:
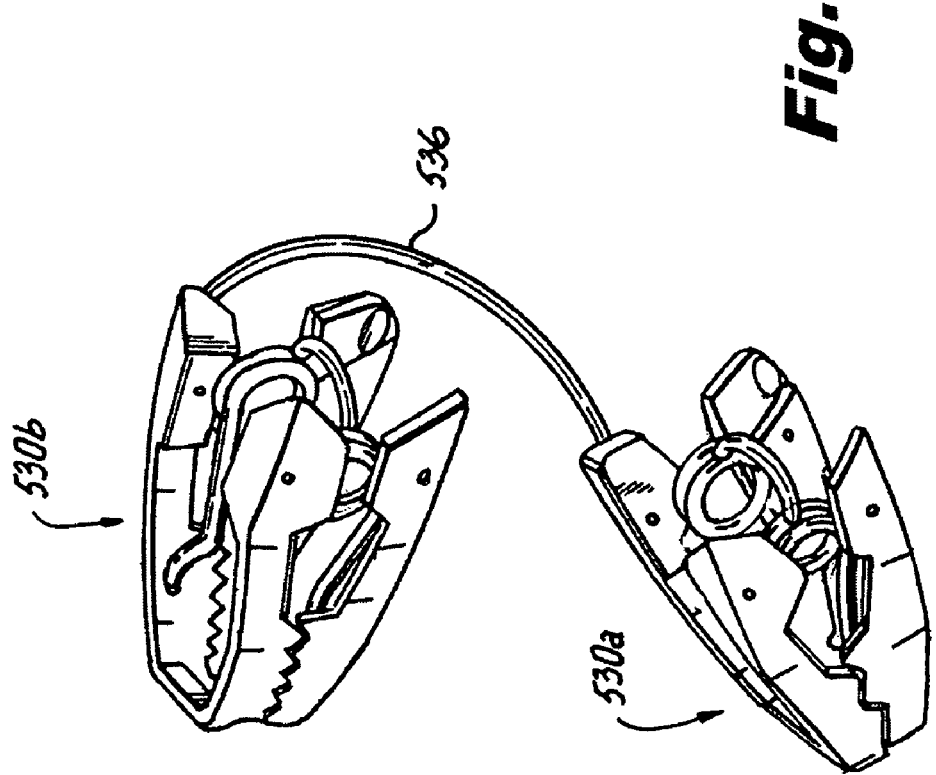

Once the first clip 530a is installed/deployed, the applicator 510 is moved adjacent to the desired location for deploying the second clip 530b. The procedure for deploying the second clip 530b is similar to that described for deploying the first clip 530a. FIGS. 21 through 23 illustrate the steps deploying the second clip 530b, which include, pregrasping the tissue with the grasper 516 (FIGS. 20 and 21); pushing the second clip 530b distally off the applicator 510 until it clamps onto the tissue (FIG. 22) and then removing the applicator 510 by opening the jaws 518a/518b of the grasper 510 (FIG. 23). FIG. 24 illustrates the retractor system 500 in the deployed configuration.

The applicator 510 can also be configured to include a mechanism for removing the anchor clips 530 from the deployed position and returning the clips to the stored position. In the embodiment shown in FIG. 25, the mechanism for removing the anchor clips 530 from the deployed position and returning the clips to the stored position includes a hook retractor 540 which is slidably disposed within the applicator.

Figure 25:
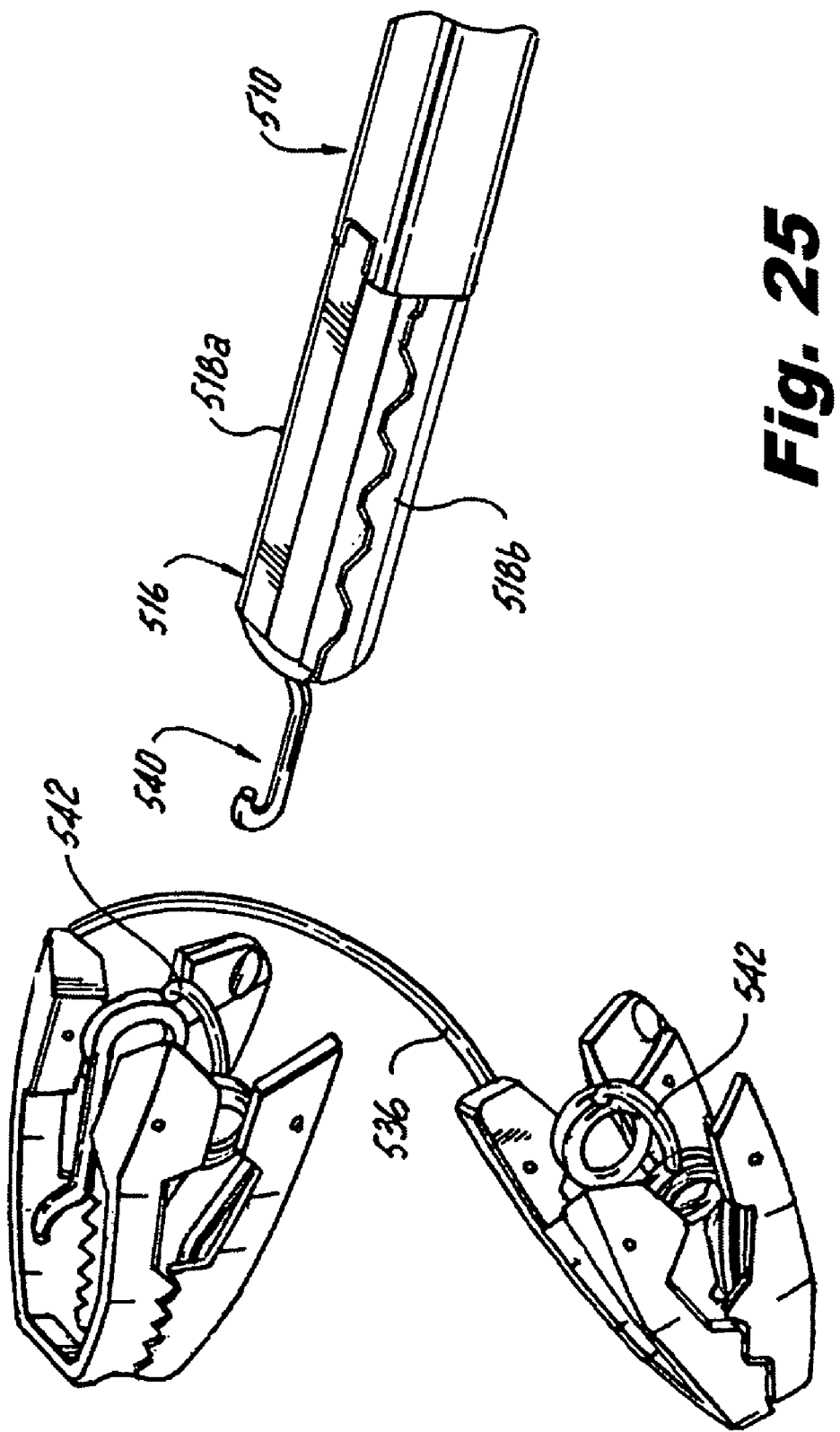
Figure 26:
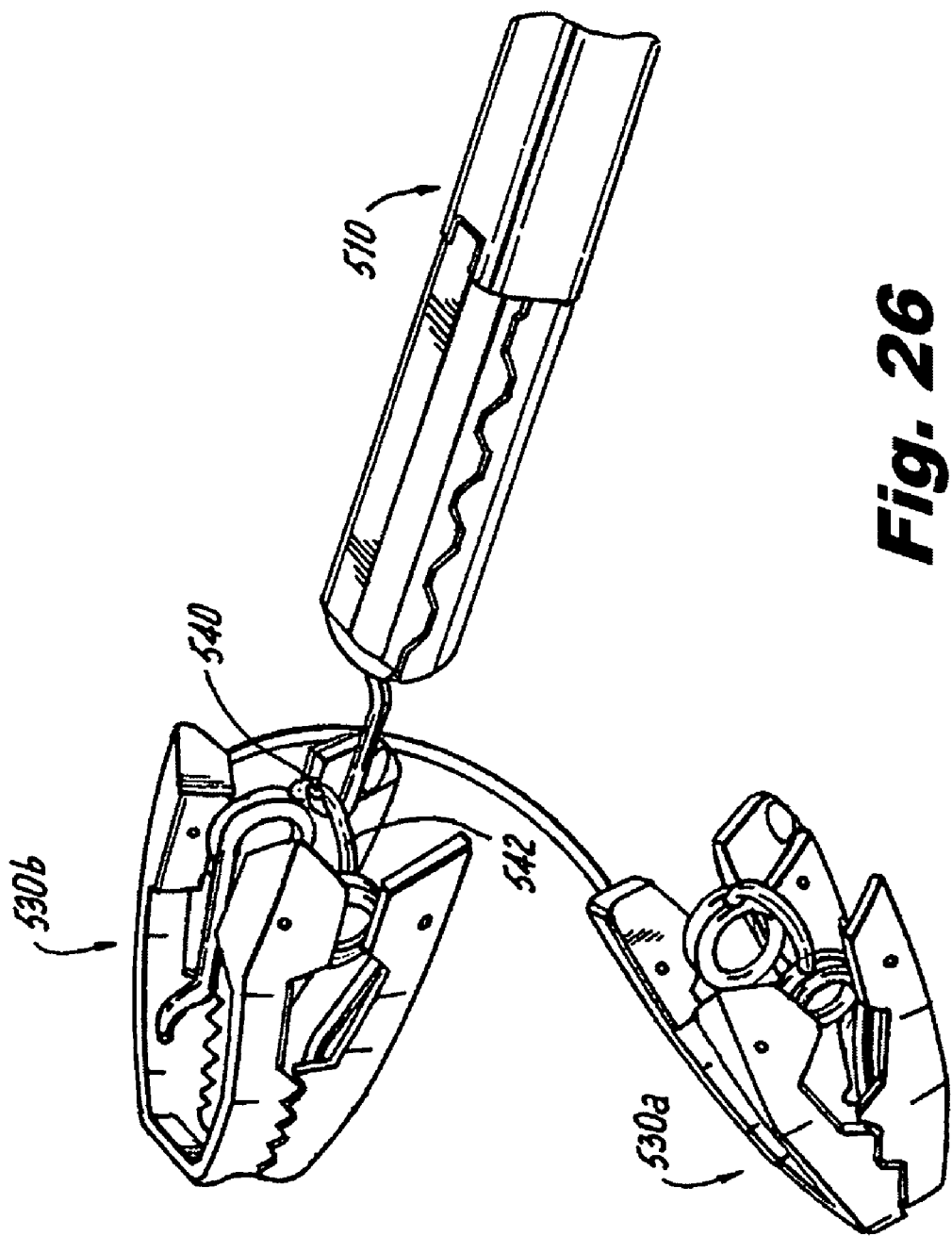
Figure 27:
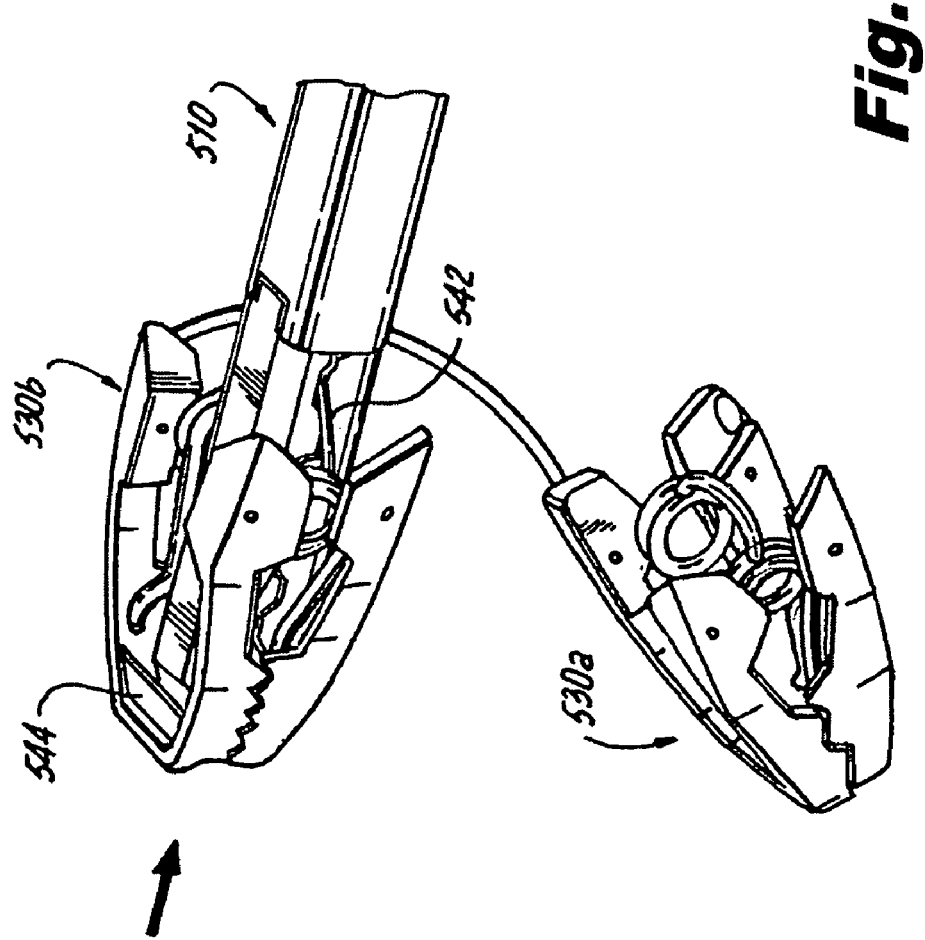
Figure 28:
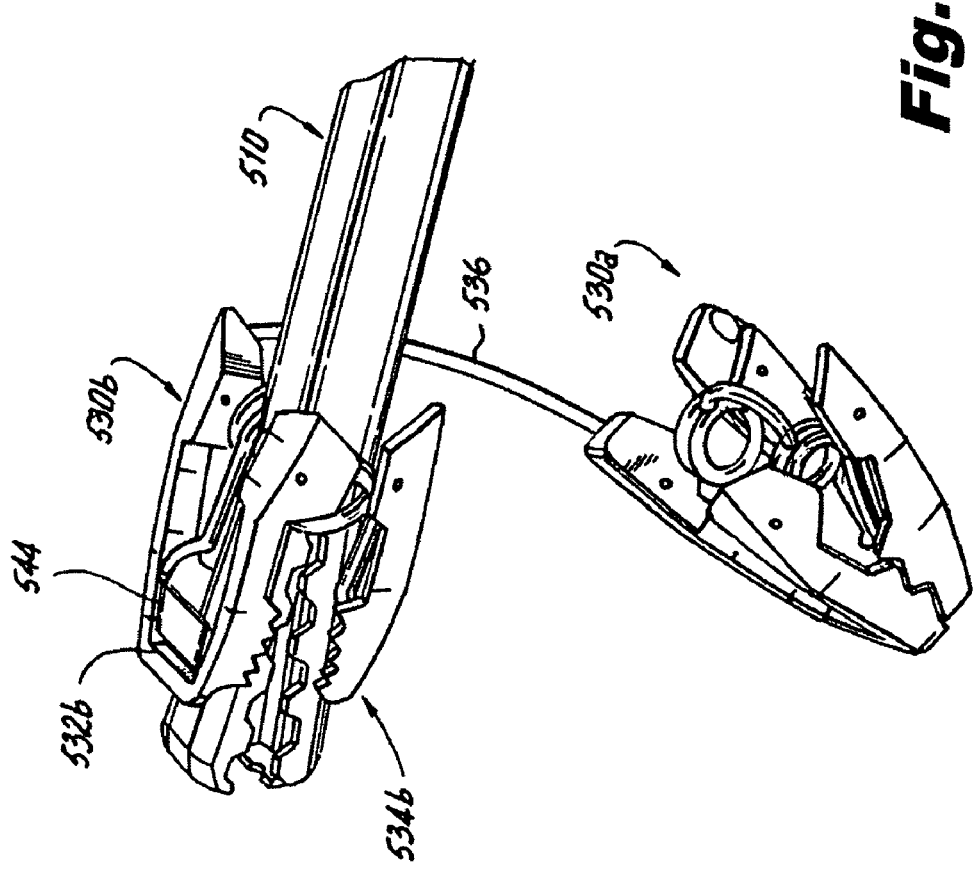
Figure 29:
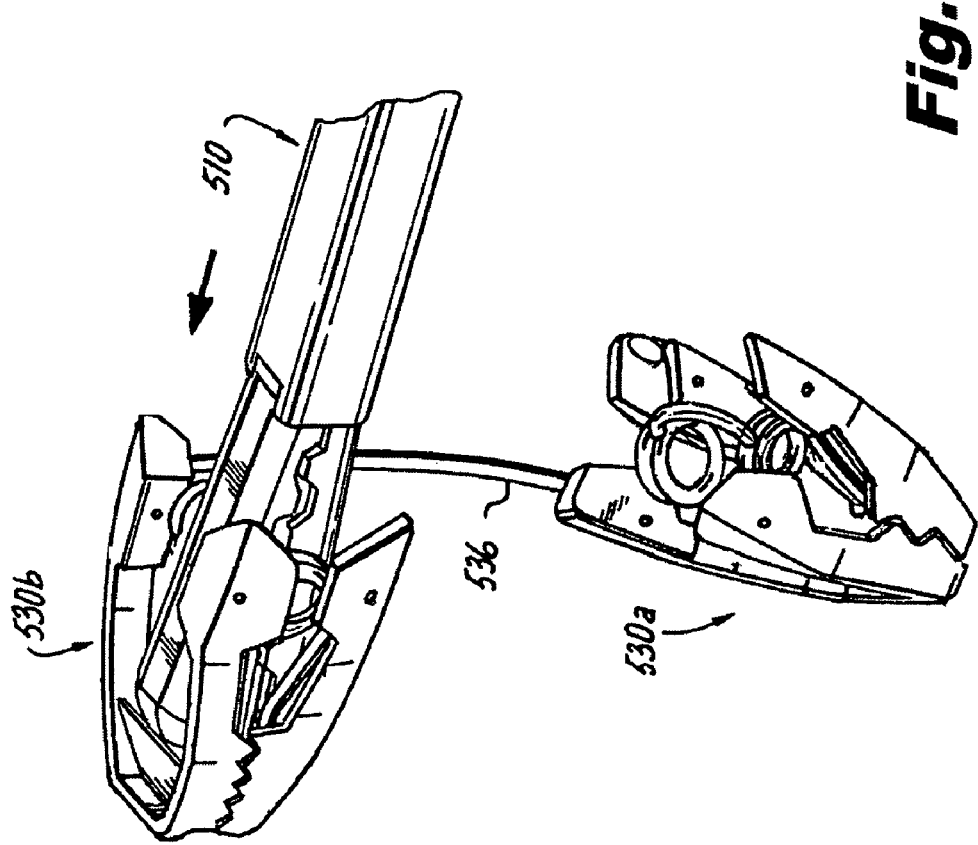
Figure 30:
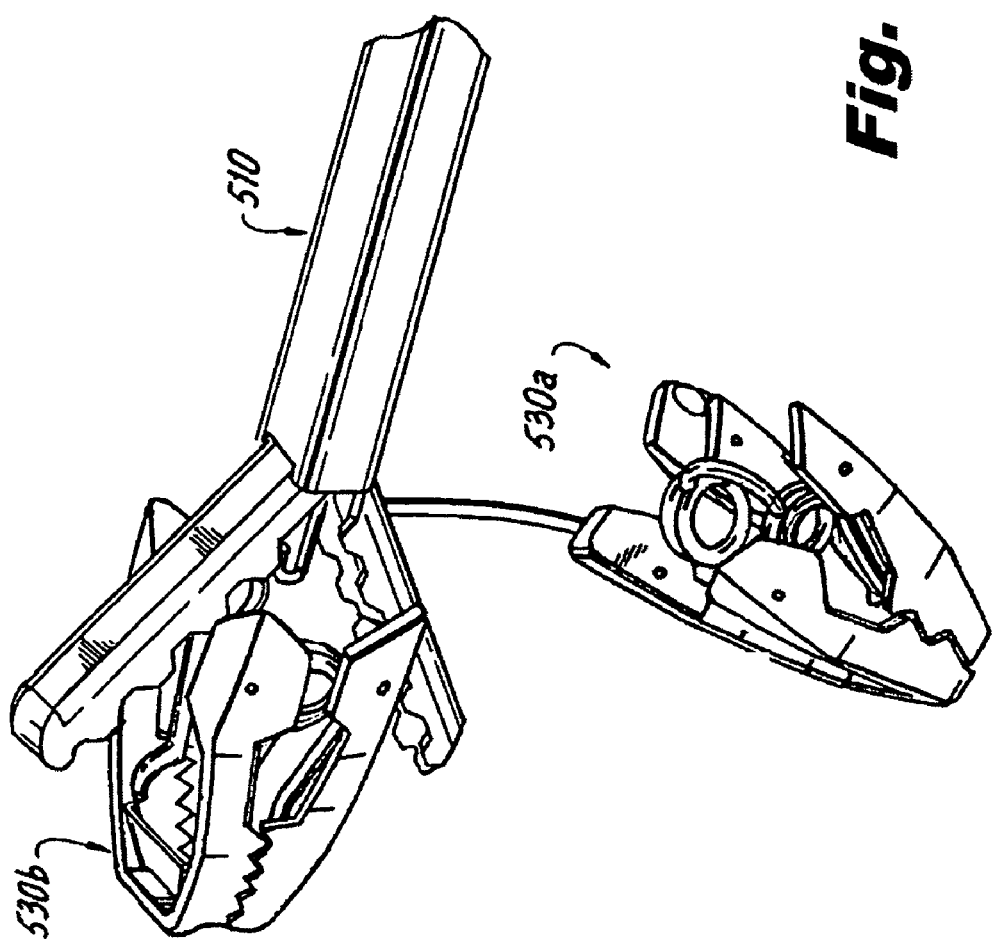

FIGS. 25 through 30 illustrate the steps for removing or relocating an anchor clip, in this case clip 530b. As shown in FIGS. 25 and 26, the hook retractor 540 is used to grab a loop 542 or other structure provided on the proximal end of each clip 530a/530b. Once the loop 542 is secured to the hook retractor 540 the grasper 516 of applicator 510 is placed into contact with clip 530b by retraction of the hook retractor 540 or through relative movement between the hook retractor 540 and the applicator 510. When the distal edge of the jaws 518a/518b of grasper 516 contact the upper 544 and lower (not shown) ramps provided on clip 530b, the jaws 518a/518b of clip 530b are pried open and the tissue is released. Clip 530b is ready to be redeployed as previously described and as shown in FIGS. 28-30 or returned to the stored position. Those skilled in the art will readily appreciate that clip 530a can also be retuned to the stored position using the hook retractor 540.

For surgical applications, the entire device must be made of materials that can be sterilized. In addition, the entire assembly must be capable of being prepackaged, sterile, in a suitable container.

What is claimed is:

1. A tissue retraction system comprising:
    an elongated applicator having proximal and distal ends, the distal end including a grasper and the proximal end including means for moving the grasper from an open position to a closed position;
    a plurality of anchor clips slidably mounted on the elongated applicator and initially in a stored position, each clip including spring biased upper and lower jaws for grasping tissue; and
    means associated with the applicator for deploying the anchor clips from the stored position to a deployed position at a desired location;
    means associated with the applicator for removing the anchor clips from the deployed position and returning the clips to the stored position.

2. A tissue retraction system as recited in claim 1, wherein two anchor clips are slidably mounted on the elongated applicator.

3. A tissue retraction system as recited in claim 2, wherein the two anchor clips are connected by a tether.

4. A tissue retraction system as recited in claim 2, further comprising an adjustable length line connecting the two anchor clips and a length adjuster configured to allow the length of the line to be adjusted unidirectionally to separate tissue and to be selectively released.

5. A tissue retraction system as recited in claim 2, further comprising a flexible line connecting the two anchor clips, having a one-way, pass-through/lock and release mechanism and a maximum-force-limit release mechanism arranged between the two anchor clips.

6. A tissue retraction system as recited in claim 5, wherein the two anchor clips are atraumatic clips.

7. A tissue retraction system as recited in claim 1, wherein the means for deploying the anchor clips from the stored position to a deployed position at a desired location includes a tubular sleeve slidably positioned over the proximal end of the elongated applicator.

8. A tissue retraction system as recited in claim 1, wherein the means for removing the anchor clips from the deployed position and returning the clips to the stored position includes a hook retractor.

* * * * *